(12) United States Patent
Fan

(10) Patent No.: US 12,272,452 B2
(45) Date of Patent: Apr. 8, 2025

(54) CARE SYSTEM AND AUTOMATIC CARE METHOD

(71) Applicant: Hao-Yi Fan, Taipei (TW)

(72) Inventor: Hao-Yi Fan, Taipei (TW)

(*) Notice: Subject to any disclaimer, the term of this patent is extended or adjusted under 35 U.S.C. 154(b) by 439 days.

(21) Appl. No.: 17/197,350

(22) Filed: Mar. 10, 2021

(65) Prior Publication Data

US 2021/0287792 A1 Sep. 16, 2021

(30) Foreign Application Priority Data

Mar. 11, 2020 (TW) ................. 109108052

(51) Int. Cl.
*G06Q 10/00* (2023.01)
*G16H 40/63* (2018.01)
*G16H 50/20* (2018.01)

(52) U.S. Cl.
CPC ............ *G16H 40/63* (2018.01); *G16H 50/20* (2018.01)

(58) Field of Classification Search
CPC ............................... G16H 40/63; G16H 50/20
See application file for complete search history.

(56) References Cited

U.S. PATENT DOCUMENTS

| 7,983,933 B2* | 7/2011 | Karkanias | G16H 10/20 |
| | | | 382/128 |
| 2019/0197861 A1* | 6/2019 | Tunnell | A61B 5/0205 |
| 2019/0228628 A1 | 7/2019 | Droscher et al. | |
| 2020/0289033 A1* | 9/2020 | Sivertsen | A61B 5/747 |
| 2021/0401365 A1* | 12/2021 | Höynälä | G08B 21/0225 |

FOREIGN PATENT DOCUMENTS

| CN | 104523263 A | 4/2015 |
| KR | 101962238 B1 | 3/2019 |
| TW | 200832273 A | 8/2008 |
| TW | M537277 U | 2/2017 |
| TW | M585969 U | 11/2019 |
| WO | WO2019063882 A1 | 4/2019 |
| WO | WO2019103620 A2 | 5/2019 |

* cited by examiner

*Primary Examiner* — Rajesh Khattar
(74) *Attorney, Agent, or Firm* — Li & Cai Intellectual Property (USA) Office

(57) ABSTRACT

A care system and an automatic care method are provided. The care system is suitable for a care recipient. A physiological condition of the care recipient can be determined by sensors arranged around the care recipient, and a health condition of the care recipient can be determined through monitoring sleep disorders thereof. The care system receives a sound of the care recipient through a sound receiver, after removing a background sound, a sound of the care recipient can be obtained, and an image sensor is used to obtain an image of the care recipient to perform a motion detection, so as to obtain a posture image of the care recipient. Artificial intelligence technology can be used to build a care-taking warning prediction model to determine whether or not the status of the care recipient has reached a warning threshold.

13 Claims, 8 Drawing Sheets

CARE SYSTEM AND AUTOMATIC CARE METHOD

CROSS-REFERENCE TO RELATED PATENT APPLICATION

This application claims the benefit of priority to Taiwan Patent Application No. 109108052, filed on Mar. 11, 2020. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a care system and an automatic care method, and more particularly to a care system and an automatic care method that monitor data of certain statuses or sleeping conditions of a care recipient, so as to achieve effects of an early warning or a reminder notification.

BACKGROUND OF THE DISCLOSURE

The conventional medical care system operates mainly by setting up physiological sensors on or around the care recipient, and the physiological sensors are connected to a care center through a network which allows the care center to obtain the physiological information transmitted by the terminal physiological sensor at any time, such that a physiological status of the care recipient can be determined.

Moreover, whether or not the conventional medical care system can achieve the purpose of caring for the care recipient depends on the immediate determining ability of the care center and the physiological data provided by the physiological sensor of the care recipient. However, the physiological sensors are often worn on the care recipient, which the physiological sensors can only provide limited physiological information, and various physiological data are independently interpreted. In addition, the method for accurately determining the physiological status should also be based on past medical records of the care recipient, current environmental factors, and the collected physiological data, such that the physiological status is comprehensively determined. The current technology is incapable of effectively implementing the method for accurately determining the physiological status.

Furthermore, regarding various types of the physiological data, professional doctors are required to make decisions based on experience thereof, but the professional doctors are still not capable of taking into account of all the possibilities. Therefore, effectively generating warnings or reminders for specific situations are not possible, which causes home care to be inconvenient. Moreover, especially for home care purposes, in general, the physiological sensors are incomparable with the equipment in medical institutions, and the physiological data obtained is limited and cannot be used for an accurate interpretation of specific conditions, such as the sleep quality of the care recipient. The sleep quality of the care recipient is an important issue that affects home care. The sleep quality of the care recipient not only affects the health thereof, but also affects the quality of life of the caretaker, since the caretaker has to pay attention to the condition of the care recipients at any time.

SUMMARY OF THE DISCLOSURE

In response to the above-referenced technical inadequacies, the present disclosure provides a care system and an automatic care method.

In one aspect, the present disclosure provides a care system including a data processing unit and a plurality of sensors. The sensors are electrically connected to the data processing unit, and the sensors include a first group of sensors operating at all times and generating a first group of detection data related to a care recipient and a second group of sensors, after being activated according to a command from the data processing unit, generating a second group of detection data related to the care recipient. When the data processing unit determines that the first group of detection data reaches a first threshold, the data processing unit generates the command and activates the second group of sensors, and the second group of sensors generates the second group of detection data.

In another aspect, the present disclosure provides an automatic care method applied in a care system, the care system includes: a data processing unit and a plurality of sensors electrically connected to the data processing unit. The sensors include a first group of sensors operating at all times and generating a first group of detection data related to a care recipient and a second group of sensors, after being activated according to a command from the data processing unit, generating a second group of detection data related to the care recipient. In the automatic care method, when the data processing unit determines that the first group of detection data generated by the first group of sensors reaches a first threshold, the data processing unit generates the command and activates the second group of sensors, and the second group of sensors generates the second group of detection data.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
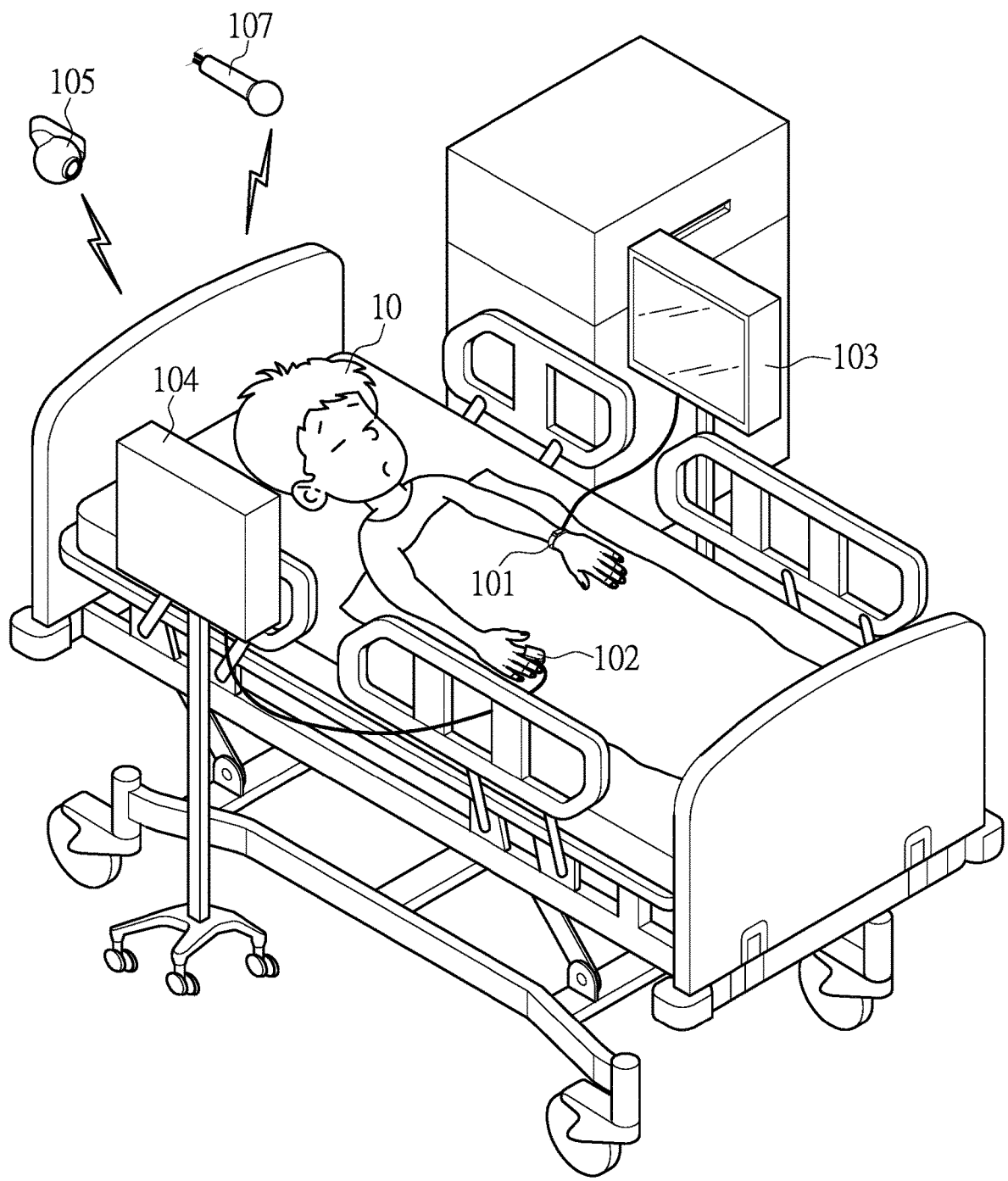
FIG. 1 is a schematic view showing a care system in operation.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

In view of the fact that a conventional care system relies on manpower (i.e., caretakers) for caring, and that providing 24-hour care services may be required under certain circumstances, a great burden on household caretakers has been brought by the manpower demand in medical institutions and hospitals. Even with care assistances from various sensor technologies, due to lacking a warning system provided according to personal physiological and environmental conditions of care recipients, frequent human attentions on the care recipients are still required to prevent the system from not being able to warn or notify of emergencies and generating false alarms making the caretakers having to frequently resolve misinformation. Therefore, a care system and an automatic care method that utilize multiple sensor technologies are provided in the present disclosure. In addition, machine learning technology is also introduced to build a care-taking warning prediction model to provide automated and personalized care warning services. One of the beneficial effects of the technical solutions of the present disclosure is to relieve conventional burdens of the caretakers and reduce the problems of only having manpower or conventional detection technologies that are limited.

One embodiment of the care system can be referred to FIG. 1, which is a schematic view showing the care system in operation.

As shown in FIG. 1, a care recipient 10 is lying in bed, at home or at a certain care center. However, since the care recipient 10 is at home or at a certain care center, there is no equivalent level of monitoring equipment to that in a hospital. Therefore, the care system is provided mainly for detecting the physiological data of the care recipient 10, and is capable of providing functions of preliminary care. Furthermore, the ability of determining the physiological condition of the care recipient from limited data can still be obtained through additional artificial intelligence technology and machine learning methods. For example, a physiological sensor, e.g., a sensor wristband 101, can be connected to the care recipient 10, and the physiological data e.g., body temperature, pulse, respiration, blood pressure, heart rate, etc., can be obtained and displayed by a corresponding physiological data display 103. Generally speaking, a warning threshold is usually set for the data, such that the functions of preliminary care can be performed. Furthermore, the system can be arranged with a blood oxygen detector 102 connected to the care recipient 10, e.g., on a finger, to obtain blood oxygen data, which can be monitored on a blood oximeter 104.

In addition, the care system may also include various types of physiological sensor devices, such as chest straps for obtaining rising and falling of a chest, a frequency of thoracic movements, and a depth of a chest of the care recipient 10 as a basis for determining a physiological status of the care recipient 10.

As shown in FIG. 1, in this embodiment, an image sensor is arranged beside the bed, such as a camera 105 shown in FIG. 1, which can film an image of the care recipient 10 at all times and execute a motion detection while filming. When performing the motion detection, a background image, including immovable objects, such as beds, wardrobes, fixed equipment, etc., can be established in advance through continuous filming, and then images filmed beforehand and afterwards can be compare to obtain changed images. The changes obtained from the images can be used to determine posture images of the care recipient 10, and the posture images can be used to obtain a behavior of the care recipient 10 and determine the condition of the care recipient 10. For example, the posture image can be used to determine whether or not the care recipient 10 has turned over, drastic changes in hands and feet within a short period of time, fell off the bed, woke up, and other actions during a sleep, which can be provided as the warning threshold for posture changes and generate a warning notification when abnormal changes occur.

Furthermore, a sound receiver, such as a microphone 107 as shown in FIG. 1, can be arranged beside the bed for receiving sounds of the care recipient 10, especially respiration-related sounds. When the microphone 107 is used to receive surrounding sounds, a background sound can be established first. The background sound is the sound generated in the surroundings, such as a sound of equipment operation, cooling fan, air-conditioning, etc. Once the background sound is established, the background sound can be removed from sounds recorded by the microphone 107, such that the sound made by the care recipient can be determined.

For example, the care system can be used to detect a quality of sleeping of the care recipient 10, and the microphone 107 is used to record a sound of the care recipient 10 when sleeping, so as to determine whether or not the care recipient 10 is in a condition requiring immediate care, such as a coughing sound, a sound of having sputum, and a breathing sound, etc., and respiration pauses can also be determined according to continuity of the sound. Therefore, the sound becomes a piece of information of high importance for determining the condition of the care recipient 10, especially the physiological conditions that are sleep related.

In addition, the physiological data of the care recipient 10 obtained through using the sensors described in the above embodiments can generate feedback information cooperative with the caretaker or the care recipient 10. Critical data at a critical period of time can be obtained through a mechanism of marking of the care system. Data generated by the care system in this embodiment are personalized data, which are different from big data required for building conventional models in traditional artificial intelligence, and can be used to build the care-taking warning prediction model based on an individual condition, and provide the personalized care warning services, and effectively relieve the burdens of the caretakers.

It is worth mentioning that the automatic care method applied in the above-mentioned care situation is capable of facilitating the physiological sensors that can detect the care recipient 10. For example, a pulse and a pulse reflected heart rate of the care recipient 10 can be detected by a sensor bracelet 101, and blood oxygen detected by the blood oxygen detector 102 allows a correlation of data between different detection data to be established, so that the condition of the care recipient 10 can be individually or comprehensively determined, and that the care recipient 10 can receive a more complete care.

Figure 2:
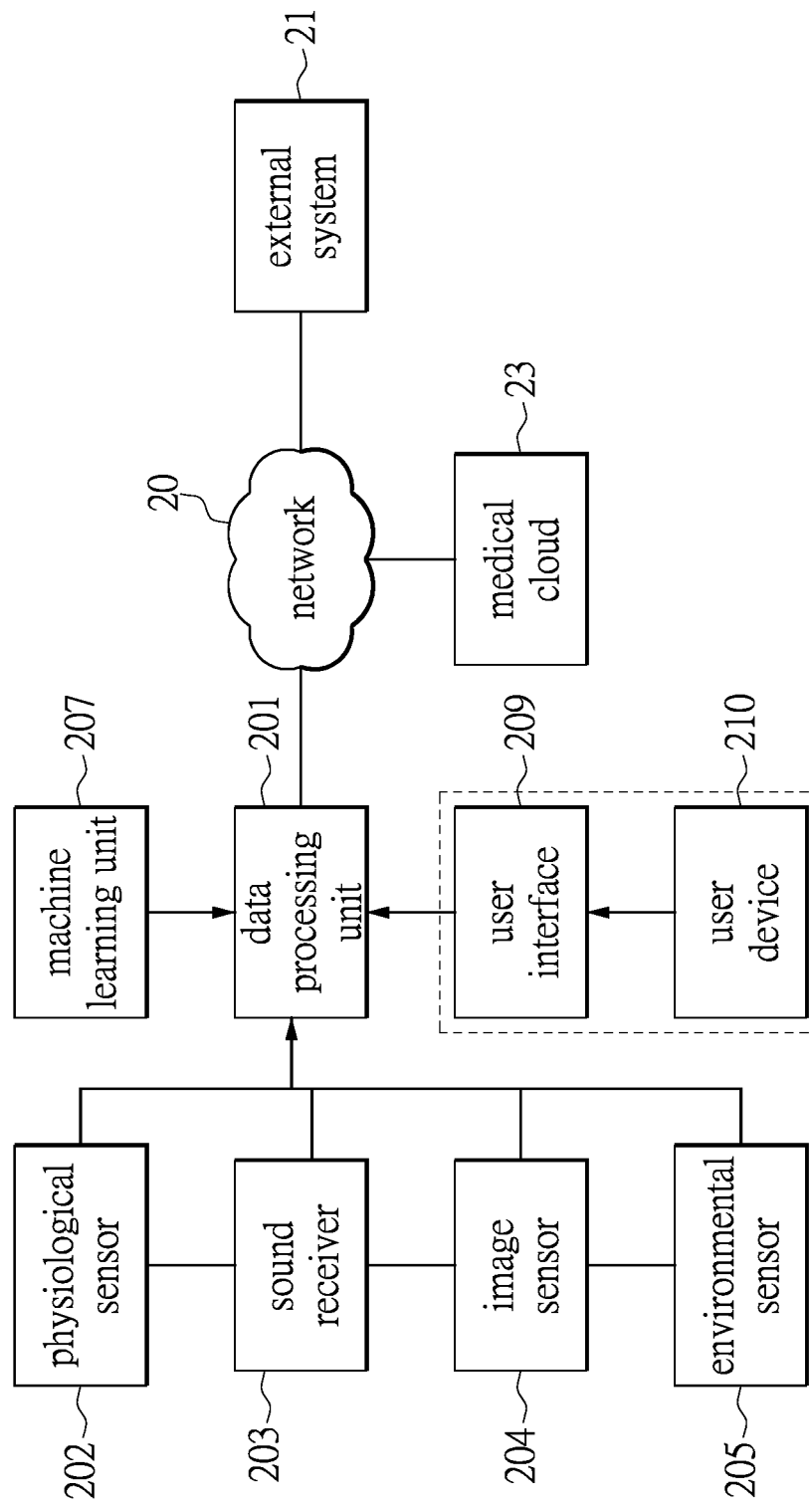
FIG. 2 is a schematic view showing each functional modules in the care system.

Referring to FIG. 2, FIG. 2 is a schematic view showing each functional modules in the care system, in which the functional modules can be achieved through software, or through a combination of software and hardware equipment.

The main components of the care system are various sensor devices around the care recipient, and a data processing unit 201 that processes data generated by each of the sensor devices is provided, such as a central processing unit of a computer system, which can have powerful data processing capability, in addition to storing the data that has been generated, can also effectively process real-time data, and can execute machine learning algorithms. After performing a big data analysis, a model for predicting the physiological condition of the care recipient can be built.

In one embodiment, the care system includes various sensors electrically connected to the data processing unit 201, which can include various types of sensors, e.g., a physiological sensor 202, a sound receiver 203, an image sensor 204, and an environmental sensor 205. In addition, the care system can include a machine learning unit 207 coupled to the data processing unit 201, and after connecting with a user device 210 through the user interface 209, the machine learning unit 207 can receive information inputted by the care recipient or the caretaker.

The care system can also be connected to an external system 21 or a medical cloud 23 through the network 20 with a certain communication protocol. In addition to providing the data of the care recipient, the care system can also obtain various clinical data, a result of an individual or a group big data analysis, etc., are used as data for the care system for implementing the artificial intelligence technology.

In the care system, the data processing unit 201, such as the central processing unit of the computer system, integrates the data generated by each peripheral devices (i.e., the sensor devices), and after the data processing unit 201 processes the data, determines whether or not to generate the warning notification, and interacts with the external system 21 (e.g., a medical institution, a care center, etc.), the medical cloud 23, etc. In addition, the care system also includes the use of artificial intelligence to build the care-taking warning prediction model to predict the physiological condition of the care recipient.

The sound receiver 203 is used to receive the sound of the care recipient. According to the above embodiment, a sound of the care recipient can be obtained through having the background sound removed from the sound of the care recipient. Therefore, in the automatic care method, the system can be obtain the sound of the care recipient according to the sound received by the sound receiver 203, and then compare sound samples (i.e., the sound of the care recipient, including a volume, a frequency, or both) to determine whether or not the care recipient requires care, such as (but not limited to) a respiratory suspension, a coughing sound, or a sound of having sputum.

The image sensor 204 is used to obtain an image of the care recipient to execute the motion detection. According to the automatic care method described in the above embodiment, the posture image of the care recipient is determined at all times while filming (i.e., a full-time recording/the continuous filming), and the motion detection is then performed. In one embodiment, a result of the motion detection provided by the image sensor 204 can be used as an activation basis of whether or not to execute a receiving and a determination of the sound. For example, when, from the image, the care recipient is determined to have started sleeping, the full-time recording is continued and the determination of the posture changes during sleep is continuously executed. At this time, when a variation of the image of the care recipient exceeds a threshold, the sound receiver 203 is activated to receive the sound of the care recipient. The variation of the image can indicate a sleep disturbance, including a respiratory distress, or a status of the care recipient that requires or does not require an intervention of the caretaker. Afterwards, the care system can determine the condition of the care recipient based on the sound (which is obtained from the care recipient) and determine whether or not the sound of the care recipient reaches the warning threshold. When the warning threshold is reached, it is indicated that the sound indicates that the care recipient is in a dangerous and distressed condition, such as having a severe respiratory suspension or in a condition of being out of breath, and the warning notification is then generated.

Therefore, the care system can perform care tasks at home or under certain circumstances according to the sound receiver 203 and the image sensor 204 arranged around the care recipient. Furthermore, the care system may also include one or more physiological sensors 202 to detect the physiological status of the care recipient and then generate the physiological data, such as body temperature, pulse, respiration, blood pressure, heart rate, etc. In practice, the care system is not limited to the physiological sensors and the data obtained. In the automatic care method executed by the data processing unit 201, after receiving the physiological data, the data processing unit 201 can determine whether or not to generate the warning notification through determining physiological data individually or comprehensively.

The environmental sensor 205 can be a temperature and humidity sensor, an air quality sensor, an air pressure sensor, etc. Environmental data obtained through the environmental sensor 205 can be used to adjust the threshold for determining the physiological condition of the care recipient, since the care recipient and instruments for detecting the data may be affected by the environmental factors. For example, the care recipient is likely to feel sick in an environment having poor air quality or abnormal indoor temperature and humidity.

In one embodiment, the care system may further include a machine learning unit 207 coupled to the data processing unit 201. The machine learning unit 207 can obtain the sound and the posture images of the care recipient according to the data processing unit 201, and compare the sound and the posture images to the clinical data, so as to build the care-taking warning prediction mode through big data analysis.

Moreover, when implementing the care-taking warning prediction model through the machine learning unit 207, the data utilized in the model can also include the environmental data of the care recipient detected by the environmental sensor 205 and the physiological data generated by various types of the physiological sensors 202, which are one of the factors for the machine learning unit 207 to build the care-taking warning prediction model. When performing machine learning according to the machine learning unit 207, the care system receives the warning notification that is generated by the care recipient or the caretaker through utilizing the user device 210 through the user interface 209. The warning notification can be an instruction given by the care recipient, the caretaker, or others to a situation (i.e., certain circumstances) that the system has not determined, which also becomes one of the factors for the machine learning unit 207 to build the care-taking warning prediction model.

For example, the care system can be connected to the user device 210 through the user interface 209, and receive information inputted by the care recipient or the caretaker. That is to say, when the system utilizes the machine learning unit 207 to perform the big data analysis so as to build the care-taking warning prediction model, actual physiological feelings of the care recipient themselves can be inputted into the care system through the user interface 209 by operating the user device 210, which becomes the feedback information of the machine learning unit 207. Similarly, the caretaker can also generate and input the feedback information based on a determination of his/her own into the care system through the user interface 209 by the user device 210, so that the system can obtain information other than the data generated by the sensor, which can be used to adjust the system utilizing machine learning to build the care-taking warning prediction model.

According to one embodiment of the care system, various types of image, sound, physiological and environmental sensors are arranged on or around the care recipient, such as the physiological sensor 202, the sound receiver 203, the image sensor 204, and various types of the environmental sensors 205. When the automatic care method is executed, one or two of the sensors can be in operation at any time. For example, as shown in FIG. 2, the physiological sensor 202 (i.e., a first group of sensors), which can be processed by the data processing unit 201 of the care system and determine that when the physiological data exceeds the threshold, a warning notification is generated, that is, other sensors (i.e., a second group of sensors) under a sleep mode (i.e., a power saving mode) are activated, such that the system can receive various types of the detection data at the time being, and the data collected, including information indicating a predicted abnormal condition of the care recipient and the care recipient is indeed in an emergency state, and information not indicating a predicted abnormal condition (i.e., unpredicted abnormal condition) of the care recipient and the care recipient is in an emergency state, become important data for machine learning.

In one embodiment, for the sensors of the care system, one or more sensors (i.e., the first group of sensors) can be operating at all times. When the system determines, by signals generated by one of the sensors individually or more than one of the sensors in cooperation, that the condition of generating the warning notification is satisfied, in addition to generating the warning notification, the system activates other ones of the sensors (i.e., the second group of sensors) that are not operating at all times, so that the care system can obtain more comprehensive information of the care recipient.

For the purpose of machine learning, the care system can obtain the conditions for the first group of sensors to generate the warning notification according to a model obtained through machine learning computing modeling, such that the machine learning unit 207, as shown in FIG. 2, can obtain the data of the second group of sensors. That is to say, the feedback information generated by the care recipient and the caretaker can be used for learning, updating, or establishing the conditions for determining whether or not the care recipient is in an emergency state, and can be thereby used for building the care-taking warning prediction model. The care-taking warning prediction model can be used to predict the physiological condition of the care recipient based on limited or complete detection data.

Figure 3:
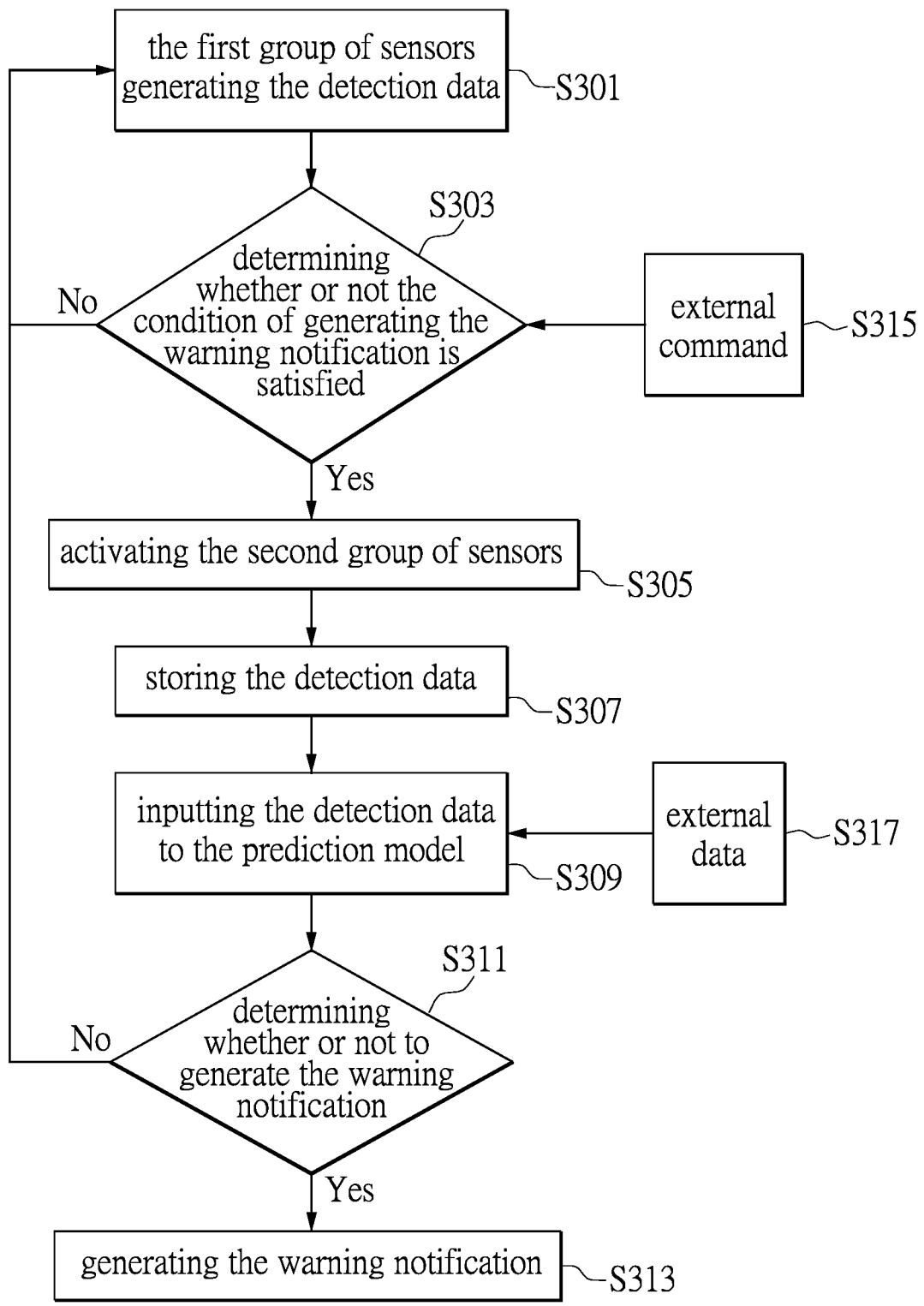
FIG. 3 is a flowchart showing an automatic care method in the care system in one embodiment.

Referring to FIG. 3, FIG. 3 is a flowchart showing an automatic care method in the care system in one embodiment. The care system includes the sensors, which are electrically connected to the data processing unit in the system, including the first group of sensors, which are operating at all times and generating the detection data of the care recipient, and the second group of sensors generate the detection data related to the care recipient, after being activated according to the command from the data processing unit.

When the care system is operating, the first group of sensors (which can include one or more of the sensors) can operate at all times, and a first group of detection data related to the care recipient is continuously generated (step S301), and the data processing unit executing the determination of whether or not the first group of detection data generated by the first group of sensors reaches the first threshold, so as to determine whether or not the condition of generating the warning notification is satisfied (step S303).

In one embodiment, in a process of the automatic care method shown in FIG. 3, in addition to automatically determining whether or not the situation satisfies the first threshold for generating the warning notification, the system can also provide the user device 210, as shown in FIG. 2, so as to input external commands through the user interface 209 (step S315), to help determine whether or not a current situation satisfies the condition of generating the warning notification, so that the original determination can be corrected and the system executes or does not continue to execute the following steps. Therefore, the system can have system operation defects made up and quality of care improved, which can all be reflected in the subsequent machine learning.

When the detection data has not reached the condition of generating the warning notification (No), step S301 is still repeated, and the first group of sensors continue to operate. At this time, it should be noted that the caretaker (or a certain person) can still intervene the process the automatic care method. That is to say, even if the detection data does not satisfy the condition of generating the warning notification established by the system, when the caretaker finds out that the warning notification is still required, the user device 210, as shown in FIG. 2, can be used to set the warning notification at the stage of the automatic care method through the user interface 209, so that the process can continue, as in step S305, and the second group of sensors are activated. In addition, data generated because of the caretaker intervention of the process are still important information for the subsequent analysis and machine learning.

When the first group of detection data satisfy the condition of generating the warning notification (Yes), the data processing unit 201 generates a command to activate the second group of sensors (which can include one or more of the sensors), and then generate the second group of detection data after detecting (step S305). At this time, the second group of detection data is received by the data processing unit 201, and the data processing unit 201 determines whether the condition of generating the warning notification is satisfied. When the second group of detection data satisfy a second threshold set by another system, the warning notification is generated. In certain embodiments, since the activation of the second group of sensors indicates that the system determines that a critical moment is at present, the first group of detection data and the second group of detection data can be marked and preserved for a period of time, so as to feedback to the machine learning unit 207 when the second group of sensors are activated (as shown in FIG. 2).

Moreover, the warning notification can be generated according to the determination of the care-taking warning prediction model (i.e., the prediction model). For example, the care system can store the first group of detection data generated by the first group of sensors generated before and after the critical moment when the warning notification is generated, and also store the second group of detection data generated by the second group of sensors that are activated at the critical moment (step S307), and then input the first group of detection data and the second group of detection data can be inputted into the prediction model established through the machine learning algorithm (step S309).

According to still another embodiment, in addition to inputting the first group of detection data and the second group of detection data into the prediction model, external data can also be added (step S317), e.g., the external data provided by the external system 21 or the medical cloud 23 shown in FIG. 2. Therefore, the determination can be more comprehensive through the real time external data obtained.

The prediction model is obtained through a model established according to features of the data of the medical institutions, the medical cloud, etc., and learning the personal historical data and the clinical data of the care recipient and obtaining correlations therebetween. In addition, parameters can be optimized according to the feedback according to actual situations, such that the limited detection data can be effectively used, e.g., current data for the care recipient generated by the first group of sensors and the second group of sensors to predict the physiological condition of the care recipient, so as to determine whether or not to generate the warning notification (Step S311).

When determined that there is no emergency state through the prediction model (No), step S301 is still returned to. At this time, the first group of sensors can still be operating continuously and continuously generating the first group of detection data, and the second group of sensors are not required to operate at all times and thus return to the power saving mode. On the other hand, when it is determined that the warning notification is required to be generated (step S313), the system generates the warning notification.

Similarly, in step S311, even if it is determined that there is no emergency state, the system still provides the caretaker to set the warning notification through the user interface 209 through the user device 210, as shown in FIG. 2, including marking and preservation of the data for a period of time, to feedback to the system.

In another embodiment, except that the second group of sensors are activated only after the condition of generating the warning notification is determined to be satisfied, the first and second group of sensors can operate in the background at all times and collect the data continuously. When the first group of detection data generated by the first group of sensors is determined to have satisfied the condition of generating the warning notification, the system actively marks and stores the first and second group detection data of the first and second groups of sensors, respectively, for a period of time (such as 1 minute). The data within the period of time should be the data that are more critical and can be used for the subsequent data analysis, including being provided for machine learning.

In another embodiment, the image sensor 204, as shown in FIG. 2, in the care system can also be used as the first group of sensors that operates at all times as mentioned above. When it is determined that abnormal images and images that exceed the threshold occur, the warning notification is generated, and the other sensors start operating, the embodiment can be referred to FIG. 4.

Figure 4:
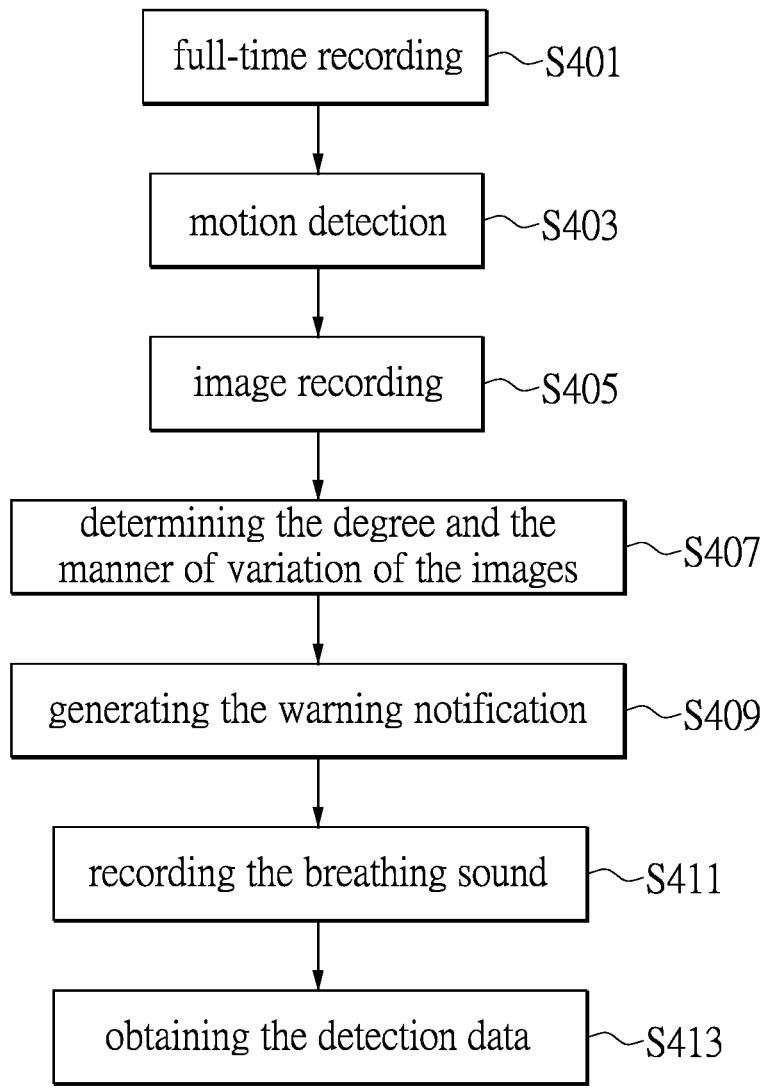
FIG. 4 is a flowchart of utilizing an image sensor to drive devices around a care recipient in one embodiment.

Referring to FIG. 4, FIG. 4 is a flowchart of utilizing an image sensor to drive devices around a care recipient in one embodiment.

When the care system adopts the image sensor and the sound receiver as the sensor device for caring the care recipient, the image sensor, such as the first group of sensors in the above-mentioned embodiments, can be used for the full-time recording (step S401), such that obtaining the images of the care recipient at every moment is possible, without having to store all the images until certain conditions of the system are satisfied. For example, during the full-time recording, the motion detection can be performed simultaneously (step S403), and the variation between the images recorded before and after can be obtained through the continuous images, and can be compared to the threshold (such as the first threshold mentioned in the above-mentioned embodiments) set by the system. The recording of the images only starts when the variation is greater than the threshold (step S405), such that a space for storing the images can be saved.

When the variation of the images is detected (i.e., a certain degree of variation is detected after the image is compared to the threshold), the degree and a manner of the variation of the image can be determined (step S407). At this time, the care system compares the degree and the manner of the variation of the images before and after to the condition of generating the warning notification, if the degree of variation and the manner indicates that the conditions of generating the warning notification is satisfied, i.e., in step S409, the warning notification is generated. At the same time, in one embodiment, the system actively marks the image, the time, and related data of a critical time (e.g., 3 minutes). For example, the posture image of the care recipient can be obtained from the motion detection of the image, and the manner of movement, such as turning over, falling, drastic body changes, etc., can be determined accordingly and possibly trigger the warning notification to be generated, and the data obtained within a critical period of time when the warning notification is generated can be preserved for other purposes. For example, the data obtained within the critical period of time can be used for the subsequent analysis and machine learning.

For example, when the warning notification is generated, i.e., when it is determined that the variation of the image of the care recipient exceeds the first threshold set by the system, the sound receiver is activated to receive the sound from the care recipient, such as step S411. The sound receiver, as the second group of sensors mentioned in the above-mentioned embodiments, starts recording breathing sound by turning on the sound receiver, e.g., a microphone. Once the background sound is removed, a cleaner sound made by the care recipient can be obtained, as shown in step S413: After obtaining and storing the sensor data in the storage device of the system, the determination is further made. Similarly, the sound recorded continuously according to the warning notification is also marked and preserved, which become reference data for the subsequent analysis and machine learning.

According to the automatic care method implemented by the care system, the condition of the care recipient can be determined from the sound, especially for sleep disorders. The sound from the care recipient can be compared with sound samples stored in the system, including frequency samples and volume samples, individualized sound samples created from past data, or sound samples generated by group data, to determine whether or not the care recipient requires immediate care, such as the respiratory suspension, a coughing sound, a sound of having sputum, or sounds of other breathing issues. When determining whether or not the warning threshold is reached (such as the second threshold in the above-mentioned embodiment), if the warning threshold is reached, such as the breathing suspension time is determined to be too long (longer than a certain time threshold), or the coughing sound or the sound of having sputum indicating that the care recipient is in a dangerous situation, etc., the warning notification is generated.

It should be noted that, the related first threshold and the second threshold can be set by the system, and the threshold of generating the warning notification can also be set by the caretaker according to the actual situations.

Furthermore, the care system can also operate cooperatively with the physiological data generated according to the physiological status of the care recipient detected by one or more of the physiological sensors (i.e., the second group of sensors), so as to further determine whether or not to generate the warning notification. Similarly, various types of the physiological data and the environmental data generated during a critical moment set by the system are marked and preserved for the subsequent analysis and machine learning.

Furthermore, the care system also adopts a machine learning method, which is able to establish a care-taking warning prediction model according to the sound and the posture images of the care recipient and having the sound and the posture images compared with the clinical data.

It is worth mentioning that, according to the automatic care method described in the above embodiments, the sound receiver can also be indicated as the first group of sensors that receive the sound of the care recipient at all times. When the sound features (e.g., a frequency, a volume, etc.) reach the threshold, the image sensor indicated as the second group of sensors are activated.

In another embodiment, recording of the sound of the care recipient can be turned on at all times. Similarly, the system can set the condition of generating the warning notification for effective sound after having the background sound removed. When the warning notification is generated, except for preserving the data of the critical moment, a program for recording the image is further activated, so as to record, mark, and preserve the images generated by the care recipient during the critical moment, which can also be used for the subsequent analysis and machine learning.

Figure 5:
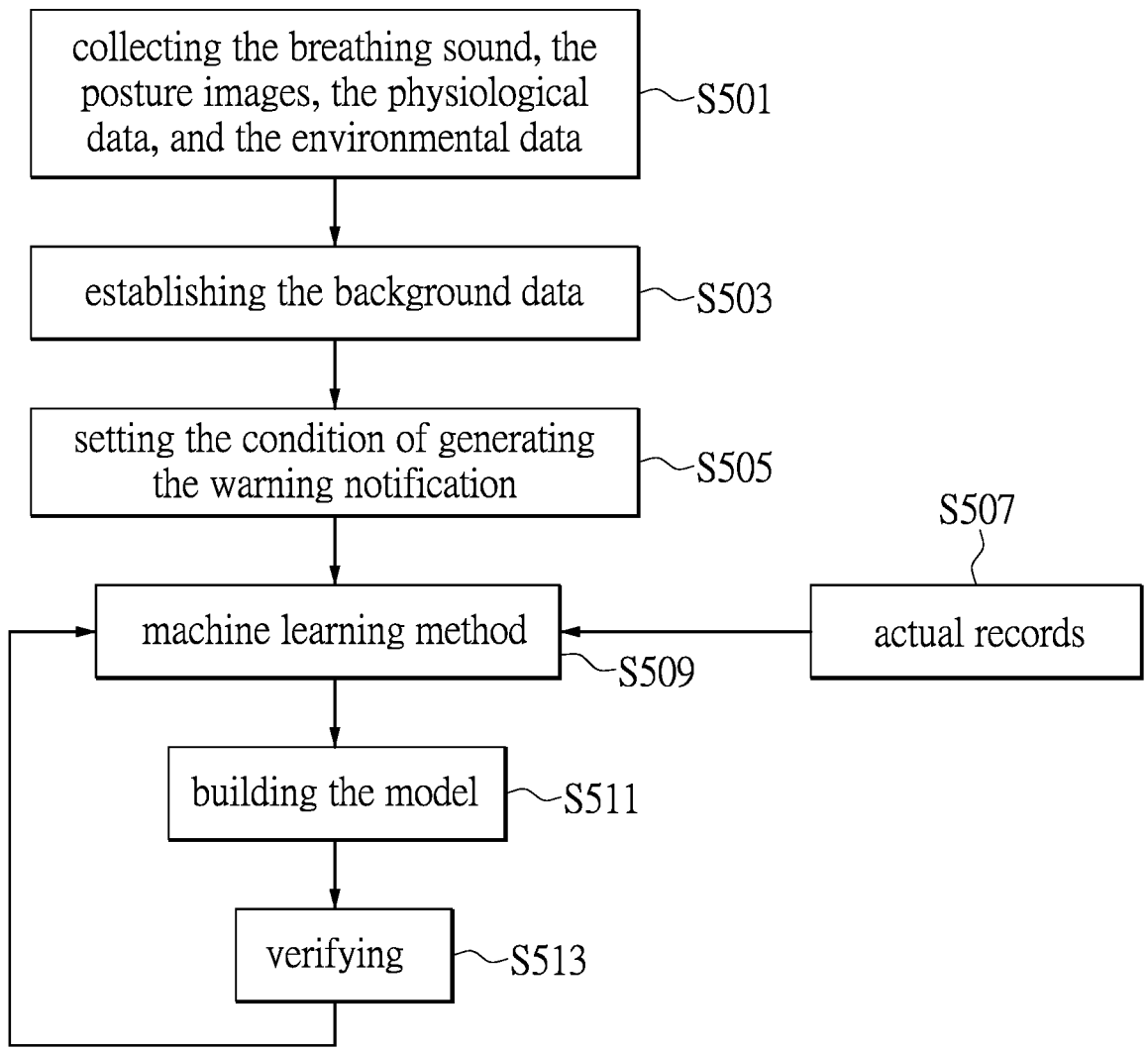
FIG. 5 is a flowchart of building a care-taking warning prediction model through a machine learning method in the automatic care method in one embodiment.

Referring to FIG. 5, FIG. 5 is a flowchart of building a care-taking warning prediction model through a machine learning method in the automatic care method in one embodiment.

In the beginning, as in step S501, the system collects the breathing sound (of the care recipient), the posture images, the physiological data, and the environmental data of the care recipient through various types of the sensors. During data processing, such as step S503, the background data has to be established first to obtain the clean data. In step S505, the system also sets the condition of generating the warning notification according to the individual situation of the care recipient. The above-mentioned are care operations in specific circumstances such as at home and in medical institutions.

In addition to continuously obtaining the breathing sound, the posture images, the physiological data, and the environmental data of the care recipient, and then obtaining the actual records, in step S507, which can come from the clinical data provided by the medical institution, the medical cloud, or the actual personal event data of the care recipient generated through the feedback mechanism in the system. Therefore, in step S509, the machine learning method starts to perform big data analysis. Generally, after the big data analysis, the care-taking warning prediction model for predicting the physiological condition of the care recipient can be built. The method of establishing the care-taking warning prediction model is built, according to the detected data generated by the sensors around the care recipient, and the actual data provided by the medical cloud, as well as the information that the care recipient and the caretaker there of actively generate through the feedback mechanism to the system, through utilizing software algorithms to learn the characteristics of the aforementioned data and establishing the correlations between the data.

In step S511, through the big data analysis and computing of the algorithms, the care-taking warning prediction model is built. In certain applications, the model can determine, according to at least one of the sound, the posture, and the physiological data detected from the care recipient during sleep, whether or not the care recipient is in a sleep disorder such as a respiratory distress, or requires intervention of the caretaker. Verification can be performed repeatedly according to actual requirements (step S513), and the parameters of the care-taking warning prediction model can be adjusted through actual data.

Figure 6:
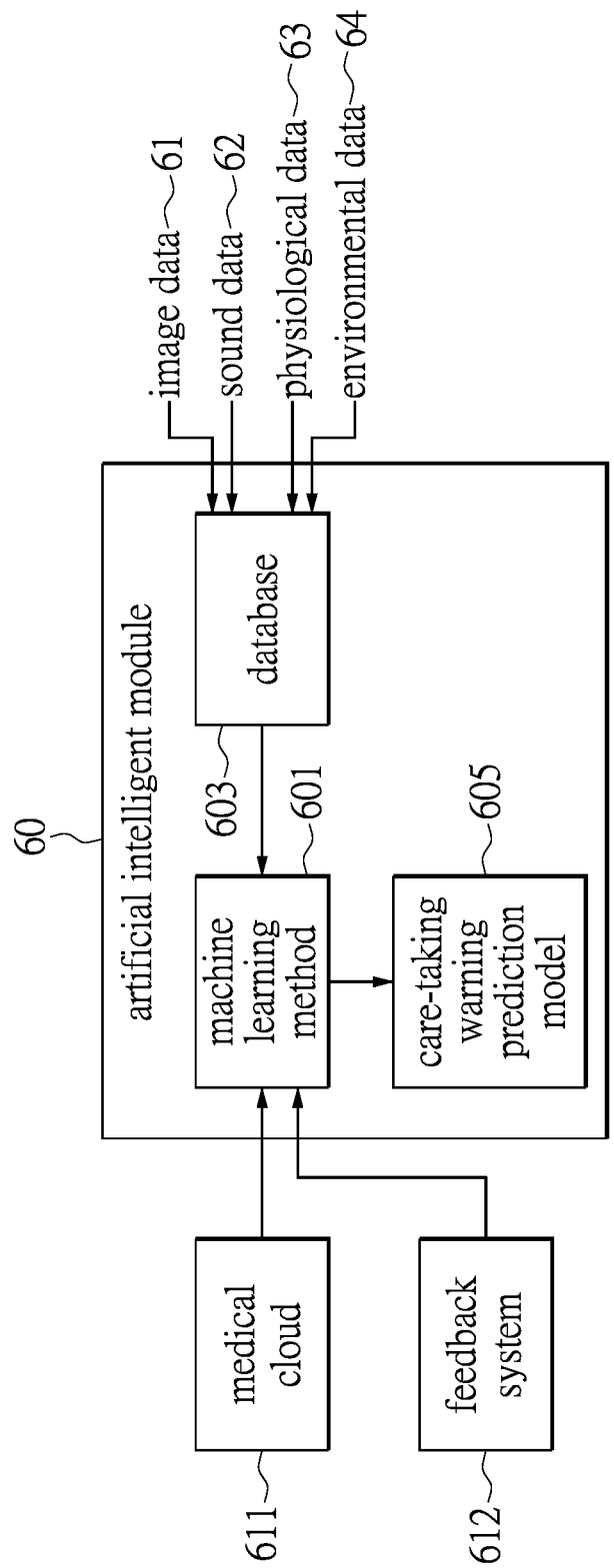
FIG. 6 is a schematic view showing the care system adopting artificial intelligent technology to build a care-taking warning prediction model in one embodiment.

Referring to FIG. 6, FIG. 6 is a schematic view showing the care system adopting artificial intelligent technology to build a care-taking warning prediction model in one embodiment.

As shown in FIG. 6, an artificial intelligence module 60 implemented through software and hardware computing capabilities is arranged in the care system, which is equipped with a machine learning method 601 that is trained according to the detection data provided by the system, and can identify the correlations between the data, so as to facilitate a purpose of predicting.

When running the machine learning method 601, the data are obtained first, e.g., a database 603 in FIG. 6 obtains image data 61 generated by the sensors. The images (i.e., the image data) include the posture (image) of the care recipient, for example, the posture such as turning over, the movement of hands and feet. Furthermore, the physiological data, such as chest fluctuation, frequency, depth, etc., can be obtained. After training, the machine method 601 can establish a recognition ability of the posture images, and establish the correlation between the posture images of the care recipient and other data. The database 603 can obtain sound data 62, such as daily routine and sleep of the care recipient, and the sound data 62 can be identified as specific physiological reactions, such as a sound of having sputum, a coughing sound, and a sound generated by the phenomenon of respiratory suspension (or respiratory distress), etc., and the correlations between the recognized sound and other data can be established. The database 603 can obtain physiological data 63, such as body temperature, heart rate, respiration, pulse, blood oxygen, etc., of the care recipient, and in addition to the normal and abnormal conditions of the physiological data, establishing the correlations between any time being and other data are required. The database 603 can also obtain the environmental data 64, through detecting the environmental data of the care recipient through the environmental sensors (which can be deemed as the first group of sensors or the second group of sensors) the environmental data becomes one of the factors of the care-taking warning prediction model 605 established by the machine learning method 601. The data can include information, such as temperature and humidity, air quality, climate, daily routine, etc., related to the care recipient, and can also establish correlation with other data through learning. The data are then analyzed, so as to find the overall correlation among the data.

It is worth mentioning that when the artificial intelligence used in the care system of the present disclosure adopts the image data 61, the sound data 62, the physiological data 63, and the environmental data 64 mentioned above, as well as other personalized data, the artificial intelligence can build a personalized care-taking warning prediction model.

After that, the machine learning method 601 used cooperative with the historical and real-time data collected by the database 603, and used cooperative with the actual recorded physiological response is able to establish personalized rules, so as to establish the care-taking warning prediction model 605 for predicting the physiological condition of the care recipient, such that what may possibly happen can be predicted based on the data before any dangerous event should occur, and that a purpose of preventing and warning in advance is achieved.

Furthermore, the artificial intelligence module 60 can also be trained and learn from the data provided by specific sources through the machine learning method 601. For example, the artificial intelligence module 60 can obtain de-identified clinical data of various groups from the medical cloud 611, and in addition to providing data required for training, the de-identified clinical data can also be used to verify the care-taking warning prediction model 605.

The artificial intelligence module 60 receives the feedback information from the care recipient, the caretaker, or generated through other methods through a feedback system 612. As mentioned in the above embodiments, the care system has the user interface that can be used to receive the warning notification of the care recipient or other people. The warning notification generated by the user device becomes one of the factors for the machine learning method 601 to establish the care-taking warning prediction model 605. The data are used to verify the prediction model and are used to adjust the parameters of the care-taking warning prediction model 605 in the artificial intelligence module 60.

In this way, the machine learning method 601 arranged in the artificial intelligence module 60 integrates various types of the data obtained by the care system through the data processing unit 201, and the machine learning method 601 can set different weights for different types of the data according to the requirements thereof, as well as the personalized data and the data from a medical cloud 611 and the feedback system 612, so as to perform the big data analysis that builds the care-taking warning prediction model 605, which is used to determine whether or not the condition of the care recipient reaches a specific warning threshold, which is also the condition of generating the warning notification.

It is worth mentioning that the medical cloud 611 can also obtain terminal data from the care system. In this way, information with de-identified markings can be obtained by the computing technology in the medical cloud 611, including time information, identity information, and the related physiological data and environmental data can be collected simultaneously, which have established the data with the markings, and are obviously related information of the medical cloud 611 and the artificial intelligence module 60 of the care system.

The physiological data and various types of the data that are marked are one of the effective data that are required to be learned through the artificial intelligence technology, so that the constructed model can identify and predict the physiological information, and continues the machine learning and the verification during the operation process to achieve a more comprehensively constructed medical cloud 611.

Figure 7:
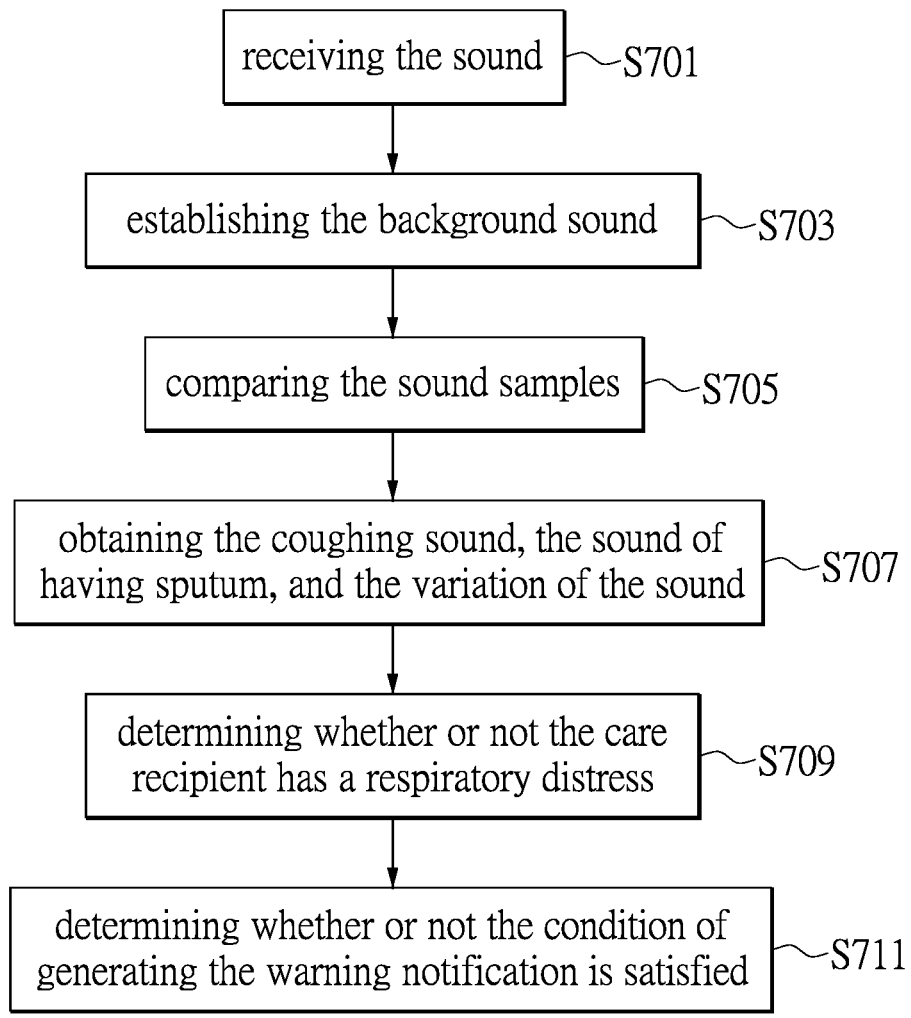
FIG. 7 is a flowchart showing the automatic care method determining a status of the care recipient according to a sound in one embodiment.

Referring to FIG. 7, FIG. 7 is a flowchart showing the automatic care method determining a status of the care recipient according to a sound in one embodiment.

At the beginning, in step S701, the sound receiver in the care system receives the sound around the care recipient. In step S703, the background sound can be established in the initial state to form the background sound sample for the system to introduce during actual operation. After that, the clean sound can be obtained.

In step S705, through software, the data processing unit 201 in the care system compares the obtained clean sound with the pre-established background sound sample, and after comparing the sound characteristics (such as a frequency, a volume, etc.), in step S707, the data processing unit 201 can recognize the sound made by the care recipient, such as a coughing sound, a sound of having sputum, and the sound variations. The sounds can be used to for a determination of the physiological condition of the care recipient, as in step S709, so as to determine whether or not immediate care is required, e.g., determine whether or not a respiratory distress (such as a breathing interruption or a coughing) occurs. Afterwards, in step S711, the threshold provided by the system is compared to determine whether or not the condition of generating the warning notification is satisfied, and subsequent medical measures can be executed accordingly.

Figure 8:
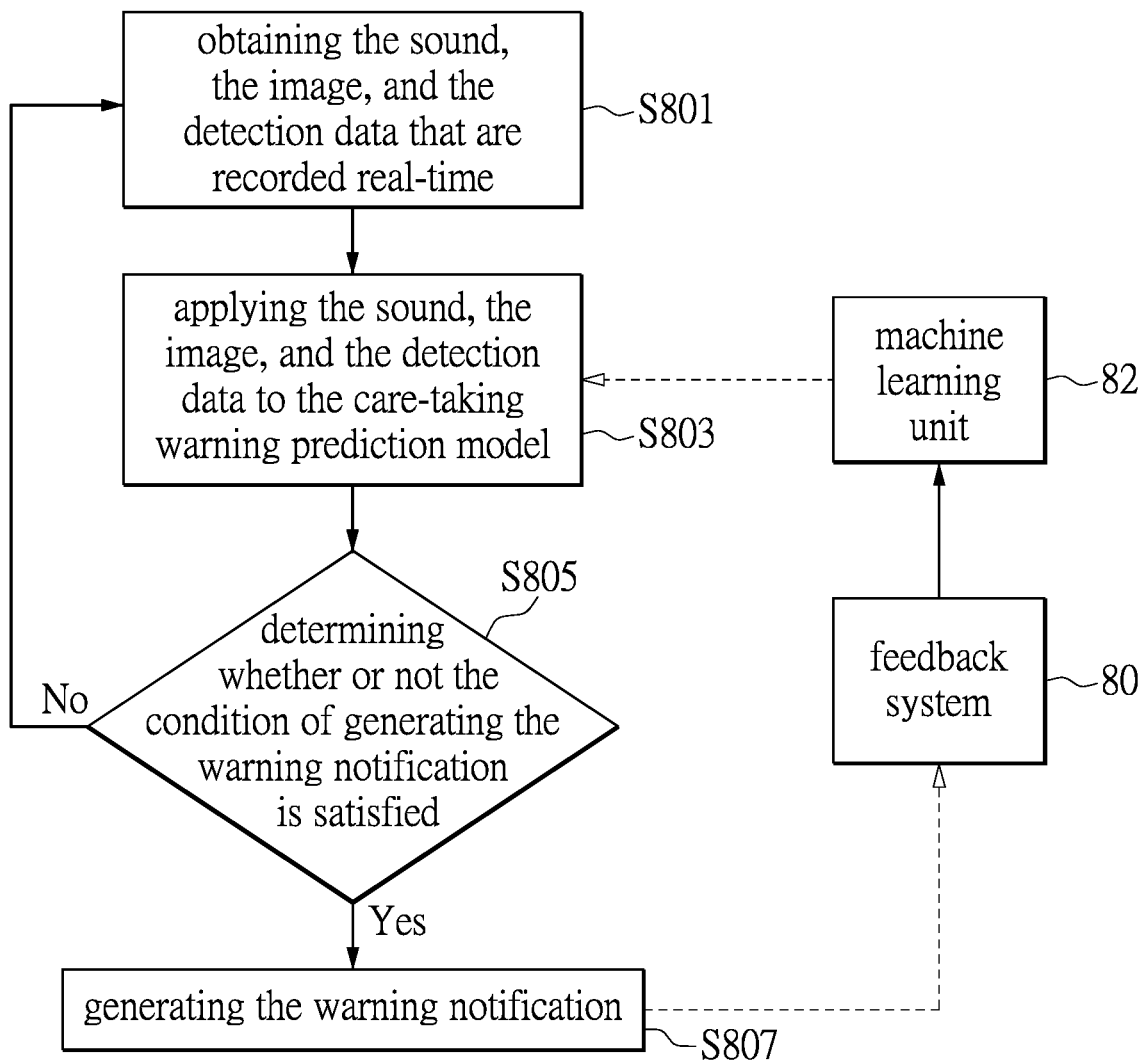
FIG. 8 is a flowchart showing the automatic care method utilizing the care-taking warning prediction model to predict an abnormal condition of the care recipient in one embodiment.

Referring to FIG. 8, FIG. 8 is a flowchart showing the automatic care method utilizing the care-taking warning prediction model to predict an abnormal condition of the care recipient in one embodiment.

In step S801, the care system obtains real time recorded sound, image, and detection data through various sensors. In step S803, the system can first perform preliminary data processing and filtering, and then import the data into the care-taking warning prediction model. The care warning prediction model determines the current physiological condition of the care recipient according to the differences and the correlations between various data, and then executes the prediction. In step S805, the system determines whether or not the warning notification is generated, and if the condition of generating the warning notification is satisfied, step S807 is proceeded to generate the warning notification; otherwise, step S801 is returned to.

It is worth mentioning that when generating the warning notification, feedback can be provided for the care recipient related data, and information according to the actual situations can be obtained through a feedback system 80, and a machine learning unit 82 can then optimize the care-taking warning prediction model.

Beneficial Effects of the Embodiment

In conclusion, the care system and automatic care method described in the above embodiments are applicable to the care environment with people requiring care. In the automatic care method, in addition using the data generated by the various sensors (e.g., various types of contacting and non-contacting sensors) in the care system to integrate various data, so as to determine the physiological condition of the care recipient, and the machine learning method can also be trained and learn from various data to obtain the correlation between the data. More specifically, through using the personalized physiological and environmental data, the personalized care-taking warning prediction model for predicting the physiological condition of the care recipient are established. Therefore, the care system and the automatic care method of the present disclosure can achieve the purpose of caring at home or in specific circumstances, and through the automatic care method or the artificial intelligence technology, the caretaker is helped to effectively care for the care recipient.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A care system, comprising:
    a data processing unit;
    a plurality of sensors electrically connected to the data processing unit, the sensors including a first group of sensors operating at all times and continuously generating a first group of detection data related to a care recipient and a second group of sensors that are activated for generating a second group of detection data wherein, after the second group of sensors are activated according to a command from the data processing unit, the second group of sensors generate the second group of detection data related to the care recipient; wherein, when the data processing unit determines that the first group of detection data reaches a first threshold that is configured to determine if an abnormal condition occurs, the data processing unit generates the command and activates the second group of sensors to generate the second group of detection data; and
    a user interface, used to interconnect with a user device and the data processing unit of the care system, for receiving a warning notification generated when the care recipient or a care taker utilizes the user device, wherein the warning notification acts as an instruction given by the care recipient or the care taker with respect to a situation that the care system has not determined, and the care system receives data other than the first group of detection data generated by the first group of sensors or the second group of detection data generated by the second group of sensors;
    wherein the data processing unit performs a machine learning method to establish a care-taking warning prediction model by learning comparisons between the first group of detection data and the second group of detection data with clinical data, and learning correlations between the warning notification, the detection data and any information inputted by the care recipient or the care taker via the user interface; and the care-taking warning prediction model is able to determine whether or not a status of the care recipient satisfies a condition of generating the warning notification;
    wherein, when the second group of sensors are activated to generate the second group of detection data, the second group of detection data and the first group of detection data to be generated at a same time are being marked, preserved for a period of time, and provided as feedback for the machine learning method in order to adjust the care-taking warning prediction model; and, when the warning notification is generated, the warning notification is also marked and preserved so as to become reference data for the machine learning method adjust the care-taking warning prediction model.

2. The care system according to claim 1, wherein, when the data processing unit receives the second group of detection data, the data processing unit determines whether or not the condition of generating the warning notification is satisfied according to a second threshold.

3. The care system according to claim 2, wherein the sensors further include:
    at least one sound receiver electrically connected to the data processing unit, so as to receive a sound of the care recipient, and remove a background sound to obtain a sound of the care recipient; and
    at least one image sensor electrically connected to the data processing unit, so as to obtain an image of the care recipient, and then perform a motion detection to the image of the care recipient, so as to obtain a posture image of the care recipient;
    wherein the at least one image sensor is the first group of sensors, and the at least one sound receiver is the second group of sensors; wherein the data processing unit executes an automatic care method, including:
        executing the motion detection through the at least one image sensor filming the posture image of the care recipient at all times; and
        activating, when a variation of the image of the care recipient exceeds the first threshold, the at least one sound receiver to receive the sound obtained from the sound of the care recipient, determining, according to the sound of the care recipient, whether or not a condition of the care recipient reaches the second threshold, and when the second threshold is reached, generating the warning notification.

4. The care system according to claim 3, wherein the second group of sensors further include one or more physiological sensors electrically connected to the data processing unit, so as to detect a physiological status of the care recipient and generate physiological data; wherein, in the automatic care method executed by the data processing unit, the data processing unit determines whether or not to generate the warning notification after receiving the physiological data.

5. The care system according to claim 3, wherein, in the automatic care method, the sound of the care recipient is compared to a sound sample including a volume, a sound frequency, or both, so as to determine whether or not the care recipient is in a condition of requiring immediate care.

6. The care system according to claim 1, wherein the sensors further include an environmental sensor for detecting environmental data of the care recipient, and the environment data becomes one of a plurality of factors of the care-taking warning prediction model.

7. An automatic care method, performed in a care system, comprising:
operating a first group of sensors that are electrically connected with a data processing unit of the care system at all times for continuously generating a first group of detection data related to a care recipient;
operating a second group of sensors, which are electrically connected with the data processing unit of the care system and are activated according to a command from the data processing unit, for generating a second group of detection data related to the care recipient; and
receiving, by a user interface, a warning notification generated when the care recipient or a care taker utilizes a user device, wherein the user interface is used to interconnect with the user device and the data processing unit of the care system; wherein the warning notification acts as an instruction given by the care recipient or the care taker with respect to a situation that the care system has not determined, and the care system receives data other than the first group of detection data generated by the first group of sensors or the second group of detection data generated by the second group of sensors;
wherein the data processing unit generates the command for activating the second group of sensor when the data processing unit determines that the first group of detection data generated by the first group of sensors reaches a first threshold that is configured to determine if an abnormal condition occurs, and the second group of sensors generates the second group of detection data;
wherein the data processing unit performs a machine learning method to establish a care-taking warning prediction model by learning comparisons between the first group of detection data and the second group of detection data with clinical data, and learning correlations between the warning notification, the detection data and any information inputted by the care recipient or the care taker via the user interface; and the care-taking warning prediction model is able to determine whether or not a status of the care recipient satisfies a condition of generating the warning notification;
wherein, when the second group of sensors are activated to generate the second group of detection data, the second group of detection data and the first group of detection data to be generated at a same time are being marked, preserved for a period of time, and provided as feedback for the machine learning method in order to adjust the care-taking warning prediction model; and, when the warning notification is generated, the warning notification is also marked and preserved so as to become reference data for the machine learning method adjust the care-taking warning prediction model.

8. The automatic care method according to claim 7, wherein, when the data processing unit receives the second group of detection data, the data processing unit determines whether or not the condition of generating the warning notification is satisfied according to a second threshold.

9. The automatic care method according to claim 8, wherein the first group of sensors includes at least one sound receiver electrically connected to the data processing unit, so as to receive a sound of the care recipient and remove a background sound to obtain a sound of the care recipient, and the second group of sensors include at least one image sensor electrically connected to the data processing unit, so as to obtain an image of the care recipient, and then perform a motion detection to the image of the care recipient, so as to obtain a posture image of the care recipient, and wherein the automatic care method includes:
executing the motion detection through the at least one image sensor filming the posture image of the care recipient at all times; and
activating, when a variation of the image of the care recipient exceeds the first threshold, the at least one sound receiver to receive the sound obtained from the sound of the care recipient, determining, according to the sound of the care recipient, whether or not a condition of the care recipient reaches the second threshold, and when the second threshold is reached, generating the warning notification.

10. The automatic care method according to claim 9, wherein the second group of sensors further includes one or more physiological sensors, the automatic care method further receives physiological data generated through the one or more physiological sensors detecting a physiological status of the care recipient, and further determines whether or not to generate the warning notification.

11. The automatic care method according to claim 9, wherein the sound of the care recipient is compared to a sound sample including a volume, a sound frequency, or both, so as to determine whether or not the care recipient is in a condition of requiring immediate care.

12. The automatic care method according to claim 7, wherein the automatic care method determines whether or not the care recipient is in a status of respiratory distress or in a status of requiring an intervention of a care taker, according to at least one of a sound, a posture image, and physiological data generated by the care recipient when sleeping.

13. The automatic care method according to claim 7, wherein the sensors further include an environmental sensor for detecting environmental data of the care recipient, and the environmental data becomes one of a plurality of factors of the care-taking warning prediction model built by the machine learning method.

* * * * *